US008226562B2

(12) United States Patent
Pelissier et al.

(10) Patent No.: US 8,226,562 B2
(45) Date of Patent: Jul. 24, 2012

(54) HAND-HELD ULTRASOUND SYSTEM HAVING STERILE ENCLOSURE

(75) Inventors: Laurent Pelissier, Vancouver (CA); Kris Dickie, Chilliwack (CA); Kwun-Keat Chan, Vancouver (CA)

(73) Assignee: Ultrasonix Medical Corporation, Richmond (CA)

(*) Notice: Subject to any disclaimer, the term of this patent is extended or adjusted under 35 U.S.C. 154(b) by 442 days.

(21) Appl. No.: 12/188,196

(22) Filed: Aug. 7, 2008

(65) Prior Publication Data
US 2009/0043205 A1 Feb. 12, 2009

Related U.S. Application Data

(60) Provisional application No. 60/955,327, filed on Aug. 10, 2007.

(51) Int. Cl.
*A61B 8/00* (2006.01)

(52) U.S. Cl. ........ 600/446; 600/407; 600/437; 600/439; 600/443; 600/445; 600/459; 600/461

(58) Field of Classification Search .................. 600/407, 600/437, 443, 446
See application file for complete search history.

(56) References Cited

U.S. PATENT DOCUMENTS

| | | | |
|---|---|---|---|
| 5,295,485 A | 3/1994 | Shinomura et al. | |
| 5,590,658 A | 1/1997 | Chiang et al. | |
| 5,722,412 A | 3/1998 | Pflugrath et al. | |
| 5,782,767 A * | 7/1998 | Pretlow, III | 600/443 |
| 5,812,188 A * | 9/1998 | Adair | 348/77 |
| 5,817,024 A | 10/1998 | Ogle et al. | |
| 5,910,113 A * | 6/1999 | Pruter | 600/437 |
| 6,106,472 A | 8/2000 | Chiang et al. | |
| 6,132,378 A * | 10/2000 | Marino | 600/459 |
| 6,203,498 B1 | 3/2001 | Bunce et al. | |
| 6,251,073 B1 | 6/2001 | Imran et al. | |
| 6,273,252 B1 * | 8/2001 | Mitchell | 206/320 |
| 6,569,102 B2 | 5/2003 | Imran et al. | |
| 6,638,226 B2 | 10/2003 | He et al. | |
| 6,953,433 B2 | 10/2005 | Kerby et al. | |
| 7,029,178 B2 * | 4/2006 | Gzybowski | 383/64 |
| 7,115,093 B2 | 10/2006 | Halmann et al. | |
| 7,221,972 B2 | 5/2007 | Jackson et al. | |
| 2004/0138564 A1 * | 7/2004 | Hwang et al. | 600/446 |
| 2005/0059891 A1 * | 3/2005 | Kosaku | 600/439 |
| 2006/0106306 A1 * | 5/2006 | Essner et al. | 600/436 |
| 2006/0264751 A1 * | 11/2006 | Wendelken et al. | 600/439 |
| 2010/0160784 A1 * | 6/2010 | Poland et al. | 600/453 |

* cited by examiner

*Primary Examiner* — Tse Chen
*Assistant Examiner* — Jason Ip
(74) *Attorney, Agent, or Firm* — Oyen Wiggs Green & Mutala LLP

(57) ABSTRACT

A sterile enclosure is provided for enclosing a hand-held ultrasound device to prevent any material on the ultrasound device from contaminating a sterile environment in which the ultrasound device is used. The enclosure has an opening for insertion of the ultrasound device into the enclosure, a closure for closing the opening, an acoustically-transparent transducer portion for covering an active face of a transducer of the ultrasound device, and a transparent display portion overlaying a display of the ultrasound device. In some embodiments a detachable or integrally formed needle guide is provided with the enclosure, for holding and guiding a needle so that the needle is projected into a field of view of the transducer of the ultrasound device.

5 Claims, 8 Drawing Sheets

HAND-HELD ULTRASOUND SYSTEM HAVING STERILE ENCLOSURE

CROSS-REFERENCE TO RELATED APPLICATION

This application claims priority from U.S. patent application No. 60/955,327 filed 10 Aug. 2007 and entitled HAND-HELD ULTRASOUND SYSTEM HAVING STERILE ENCLOSURE. This application claims the benefit under 35 U.S.C. §119 of U.S. patent application No. 60/955,327 filed 10 Aug. 2007 and entitled HAND-HELD ULTRASOUND SYSTEM HAVING STERILE ENCLOSURE which is hereby incorporated herein by reference.

TECHNICAL FIELD

This invention relates to a hand-held apparatus for obtaining ultrasound images. Particular embodiments of the invention relate to enclosures for hand-held ultrasound imaging devices.

BRIEF DESCRIPTION OF DRAWINGS

A number of example embodiments are illustrated in the attached drawings. These example embodiments are illustrative and are not intended to be restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

This invention has a number of aspects that may be implemented separately or in [[an]] suitable combinations. The features as described herein may be combined in any suitable combinations with the features described in the commonly-owned US provisional patent applications entitled:

HAND-HELD ULTRASOUND IMAGING DEVICE HAVING RECONFIGURABLE USER INTERFACE (application No. 60/955,328);

POWER MANAGEMENT IN PORTABLE ULTRASOUND DEVICES (application No. 60/955,329);

HAND-HELD ULTRASOUND IMAGING DEVICE HAVING REMOVABLE TRANSDUCER ARRAYS (application No. 60/955,325);

WIRELESS NETWORK HAVING PORTABLE ULTRASOUND DEVICES (application No. 60/955,331); and, HANDHELD ULTRASOUND IMAGING SYSTEMS (application No. 60/977,353) all of which are hereby incorporated herein by reference. The features as described herein may also be combined in any suitable combinations with the features described in the commonly-owned US non-provisional patent applications which are filed on the same day as the instant application and entitled:

HAND-HELD ULTRASOUND IMAGING DEVICE HAVING RECONFIGURABLE USER INTERFACE (claiming priority from application No. 60/955,328);

POWER MANAGEMENT IN PORTABLE ULTRASOUND DEVICES (claiming priority from application No. 60/955,329);

HAND-HELD ULTRASOUND IMAGING DEVICE HAVING REMOVABLE TRANSDUCER ARRAYS (claiming priority from application No. 60/955,325);

WIRELESS NETWORK HAVING PORTABLE ULTRASOUND DEVICES (claiming priority from application No. 60/955,331); and HANDHELD ULTRASOUND IMAGING SYSTEMS (claiming priority from application No. 60/977,353); all of which are hereby incorporated herein by reference.

Figure 1:
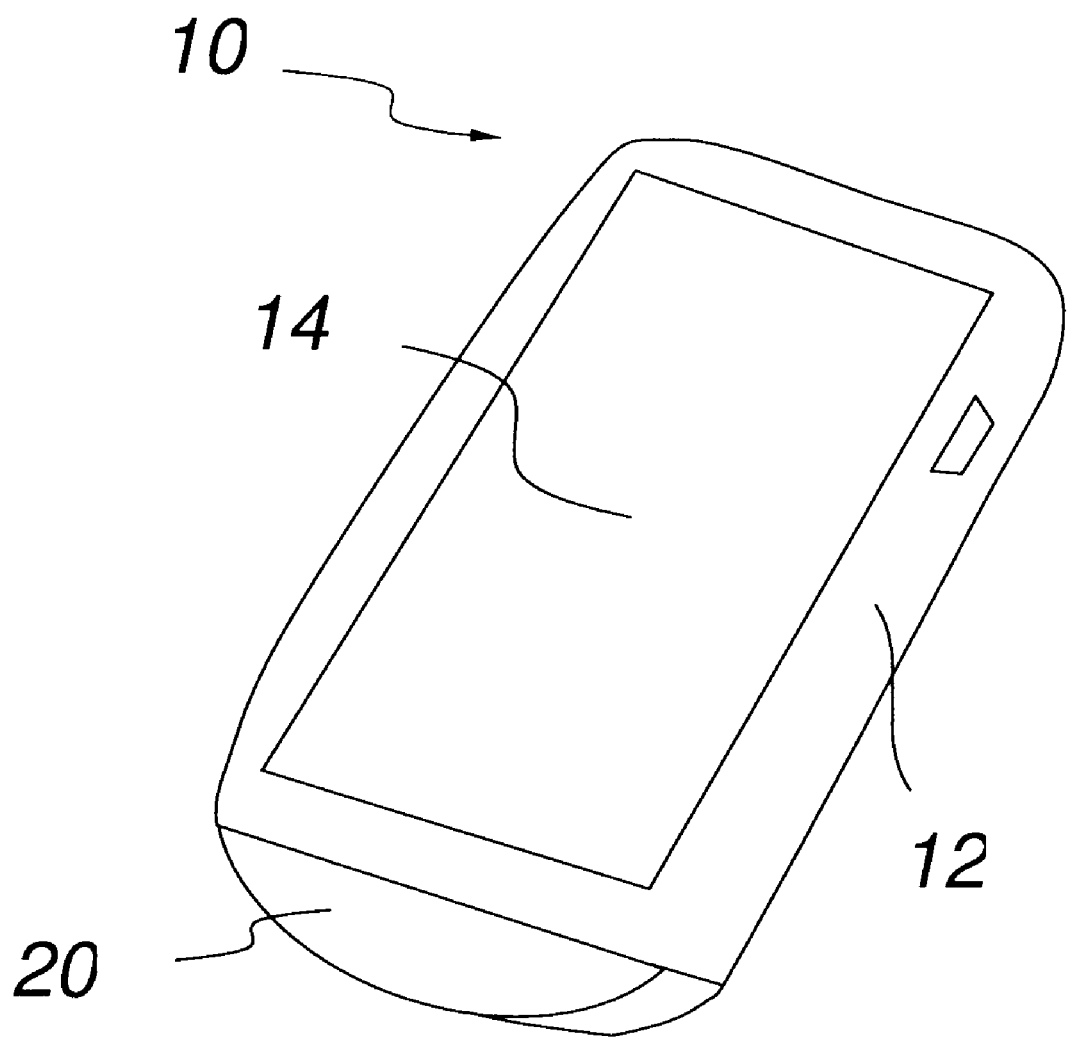
FIG. 1 shows a hand-held ultrasound apparatus.

One aspect of the invention provides a hand-held ultrasound apparatus having a removable sterile enclosure. The hand-held ultrasound apparatus may comprise a transducer, processing circuitry and a display to display ultrasound images. The hand-held ultrasound apparatus may be powered by batteries or the like. FIG. 1 shows an example hand-held ultrasound apparatus 10. Apparatus 10 comprises a display 14 on which can be displayed an ultrasound image 15. Apparatus 10 also comprises a transducer array 20.

Figure 2:
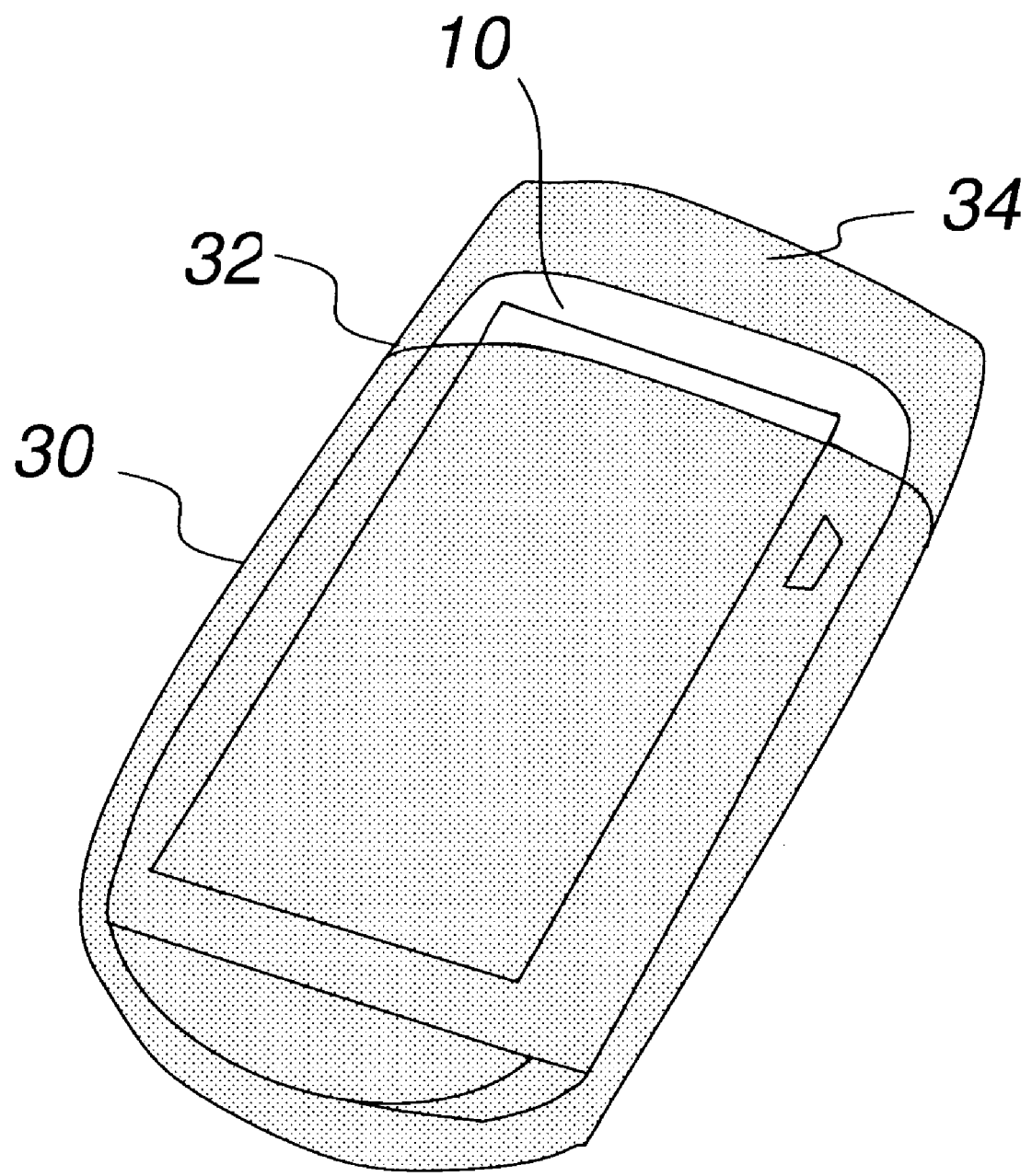
FIG. 2 shows a hand-held ultrasound apparatus like that of FIG. 1 in a sterile enclosure.

FIG. 2 shows hand-held ultrasound apparatus 10 enclosed in a sterile enclosure 30. Sterile enclosure 30 has an opening 32 through which ultrasound apparatus 10 can be introduced into sterile enclosure 30. Sterile enclosure 30 has a closure 34 which closes opening 32 after ultrasound apparatus 10 is inside enclosure 30. A number of individual features of sterile enclosures according to specific embodiments are described below. These features may be combined in various ways, including but not limited to those described below.

Sterile enclosures may comprise any suitable closure capable of closing the opening through which the hand-held ultrasound apparatus is inserted within the sterile enclosure. For example, the closure may comprise a flap which can be sealed over the opening to close the opening by way of a suitable adhesive, or a pair of adhesive flaps that may be sealed together to cover the opening. The closure may comprise a suitable zip fastener, hook and loop fastener, magnetic closure, or the like.

The sterile enclosure allows the hand-held ultrasound apparatus to be used in an environment in which sterility is to be maintained, such as an operating theater. The sterile enclosure can be changed to prevent transmission of disease from one subject to another in sterile or non-sterile surroundings. For example, the sterile enclosure may be disposed of after use and replaced with another sterile enclosure, thereby permitting the hand-held ultrasound apparatus to be used on people or animals having potentially contagious conditions without risking the transfer of disease from one person or animal to another.

The sterile enclosure includes a portion that is acoustically-transparent (i.e. substantially transparent to ultrasonic vibrations) such that the transducer can transmit ultrasonic pulses which pass through the sterile enclosure into a subject, and can receive ultrasonic pulses which are reflected at locations within the subject and pass back through the sterile enclosure to the transducer. At least those portions of the sterile enclosure which overlie the display are optically transparent such that an operator can view the display of the hand-held ultrasound apparatus while it is kept within the sterile enclosure.

The hand-held ultrasound apparatus may have various controls for adjusting its settings, turning it on or off, and the like. These controls may be actuated through the sterile enclosure either by providing touch-sensitive controls which can be operated by an operator through the sterile enclosure or controls which can sense the presence of an operator's finger through the sterile enclosure. Such controls may use any suitable modality to detect the presence of the operator's finger. In embodiments where the controls are pressure sensitive, at least the portions of the sterile enclosure overlying the controls are flexible so that forces exerted by an operator's fingers are transmitted through the sterile enclosure to actuate the controls.

A hand-held ultrasound apparatus according to the invention may also or in the alternative be made responsive to voice or other sound commands which can be transmitted to the hand-held ultrasound apparatus through the sterile enclosure. In such embodiments, the hand-held ultrasound apparatus comprises a microphone and a voice-recognition apparatus (that may comprise a suitably-programmed data processor for example).

The sterile enclosure may completely enclose the hand-held ultrasound apparatus and therefore positively prevent any material on the hand-held ultrasound apparatus from contaminating a sterile environment in which the hand-held ultrasound apparatus is used while in the sterile enclosure.

The sterile enclosure may have a variety of forms. In some embodiments, the sterile enclosure is bag-like and has an opening through which the ultrasound apparatus can be inserted into the interior of the sterile enclosure. A closure is provided to close the opening. Means may be provided to tighten the bag-like sterile enclosure around the transducer so that there are no air bubbles or the like between the transducer and the sterile enclosure.

Figure 3:
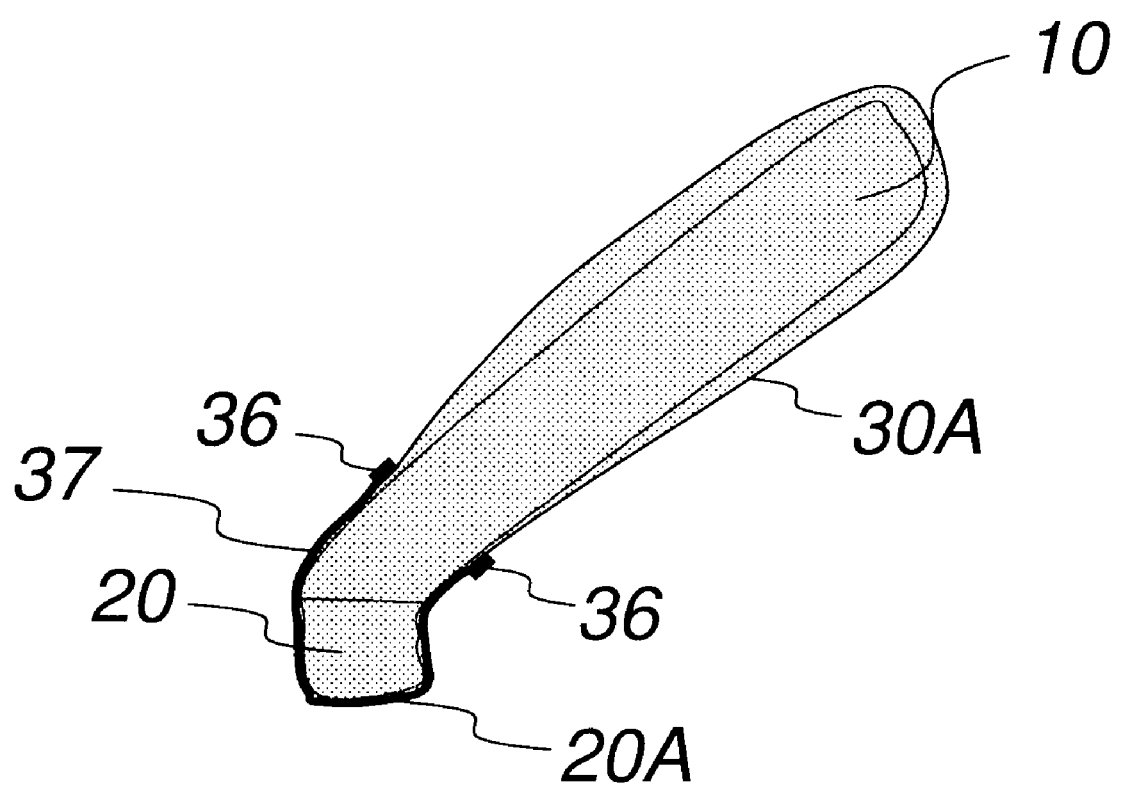
FIG. 3 is a cross section through a hand-held ultrasound apparatus in a sterile enclosure that has a bag-like configuration and is stretched over a transducer of the ultrasound apparatus.

FIG. 3 is a cross section through an ultrasound apparatus 10 enclosed in a bag-like enclosure 30A. An elastic band 36 encircles ultrasound apparatus 10 and holds a portion 37 of enclosure 30A stretched over an active face 20A of transducer array 20.

In other embodiments, the sterile enclosure comprises an elastic material that is a stretch fit over the hand-held ultrasound apparatus, or portions thereof. For example, the transparent material may comprise a transparent latex or similar material. The elastic material may stretch over the transducer and/or the display of the hand-held ultrasound apparatus.

Figure 4:
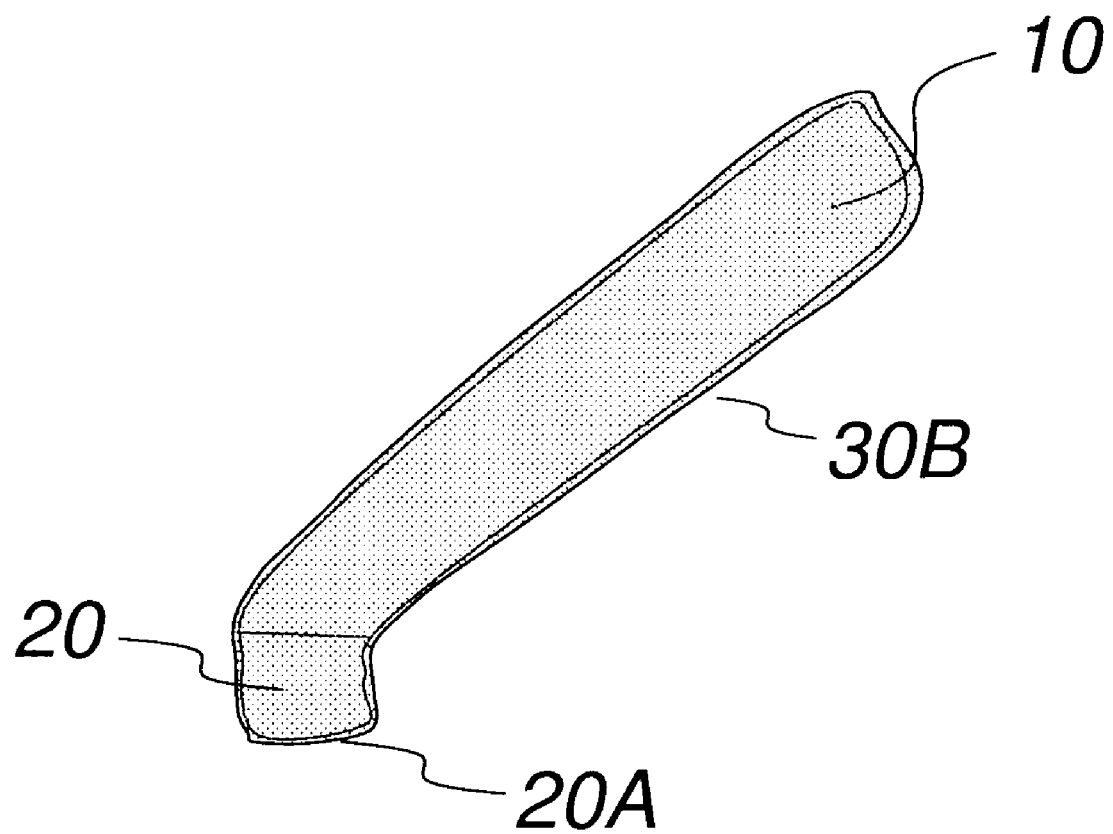
FIG. 4 is a cross section through a hand-held ultrasound apparatus in a sterile enclosure of an elastic material that is stretched over a transducer of the ultrasound apparatus.

FIG. 4 is a cross section through an ultrasound apparatus 10 enclosed in an enclosure 30B comprising an elastic material. The elastic material of enclosure 30B is stretched over an active face 20A of transducer array 20.

In other embodiments the sterile enclosure has a shape that conforms to projections or other features of configuration of the hand-held ultrasound apparatus. When these projections are received in corresponding portions of the sterile enclosure they prevent the sterile enclosure from shifting relative to the ultrasound apparatus as the ultrasound apparatus is used.

The portion of the sterile enclosure that is adjacent to the ultrasound transducer on the hand-held ultrasound apparatus may be configured in a number of different ways. In some embodiments, the enclosure comprises an acoustically-transparent material that holds its shape (i.e. is semi-rigid) and has a shape that conforms to the shape of the transducer. For example, the semi-rigid material may comprise a gel material. The material may be the same material used for the gel pads, sometimes called "aqueous standoffs", that are used in ultrasonography.

In some embodiments a gel pad is built into the sterile enclosure and shaped to conform to a shape of at least an active face of the transducer. An outer surface of the gel pad (or other acoustically-transparent material) may be coated with a slippery material at least in the vicinity of the transducer so that it can slide easily over the skin of a subject.

Figure 5:
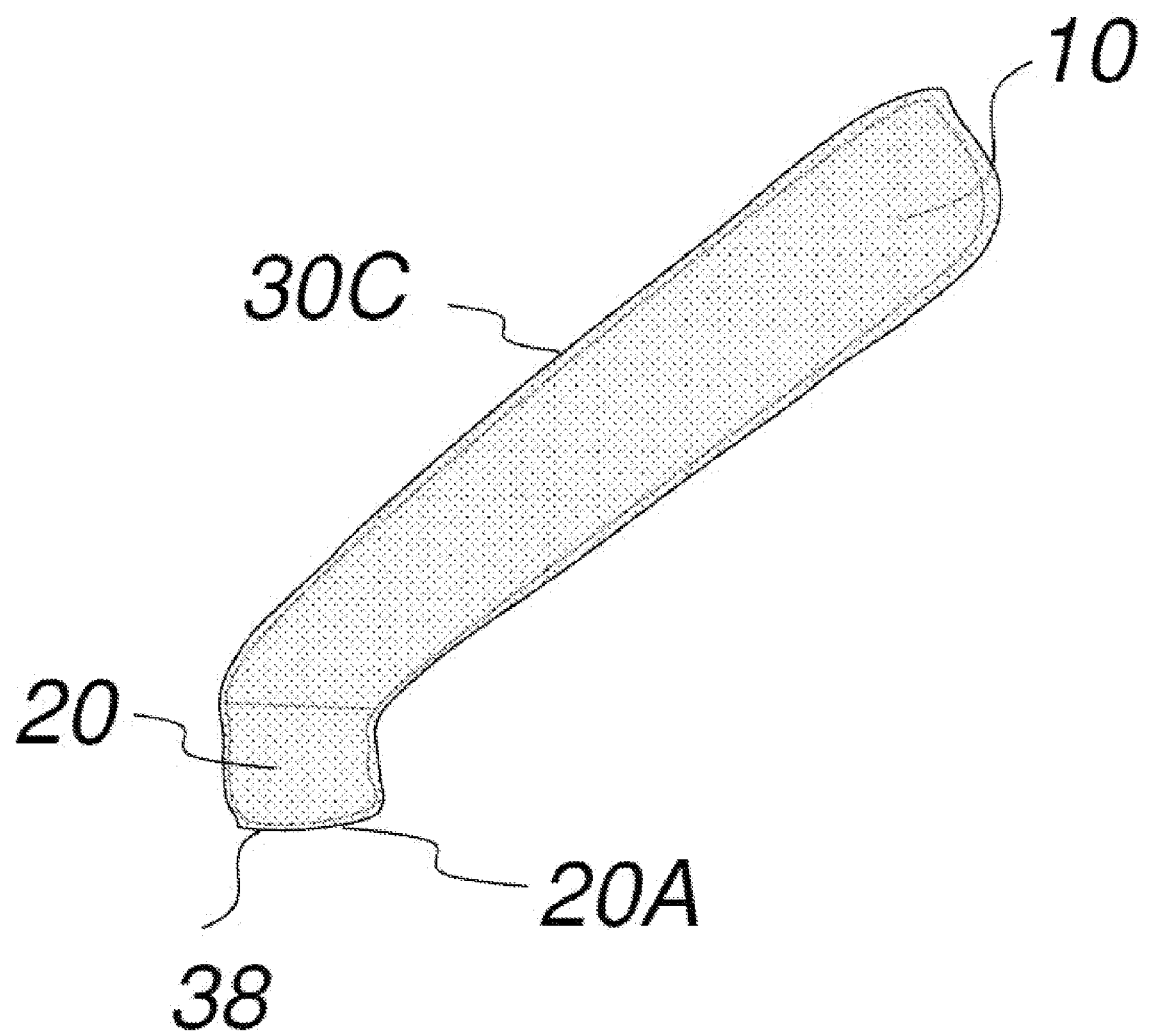
FIG. 5 is a cross section through a hand-held ultrasound apparatus in a sterile enclosure comprising a semi-rigid gel pad that is formed to conform to a transducer of the ultrasound apparatus.

FIG. 5 is a cross section through a hand-held ultrasound apparatus 10 in a sterile enclosure 30C comprising a semi-rigid gel pad 38 that is formed to conform to the active face 20A of transducer 20 of the ultrasound apparatus 10.

The gel pad may comprise projections and/or recesses that can be engaged with corresponding recesses and/or projections in the ultrasound apparatus, in order to better retain the gel pad in contact with the transducer of the ultrasound apparatus.

In other embodiments, the portion of the sterile enclosure through which ultrasound is transmitted and received may comprise a thin layer of elastic material that is a stretch fit over the transducer. In some cases, a sterile clip may be applied from the outside of the sterile enclosure to hold the material stretched over the active face of the transducer.

In some embodiments, an acoustic gel may be provided between the transducer and the inside of the sterile enclosure. The sterile enclosure may be provided with the acoustic gel already in place. The acoustic gel may be covered by a removable strip or the like.

Figure 6:
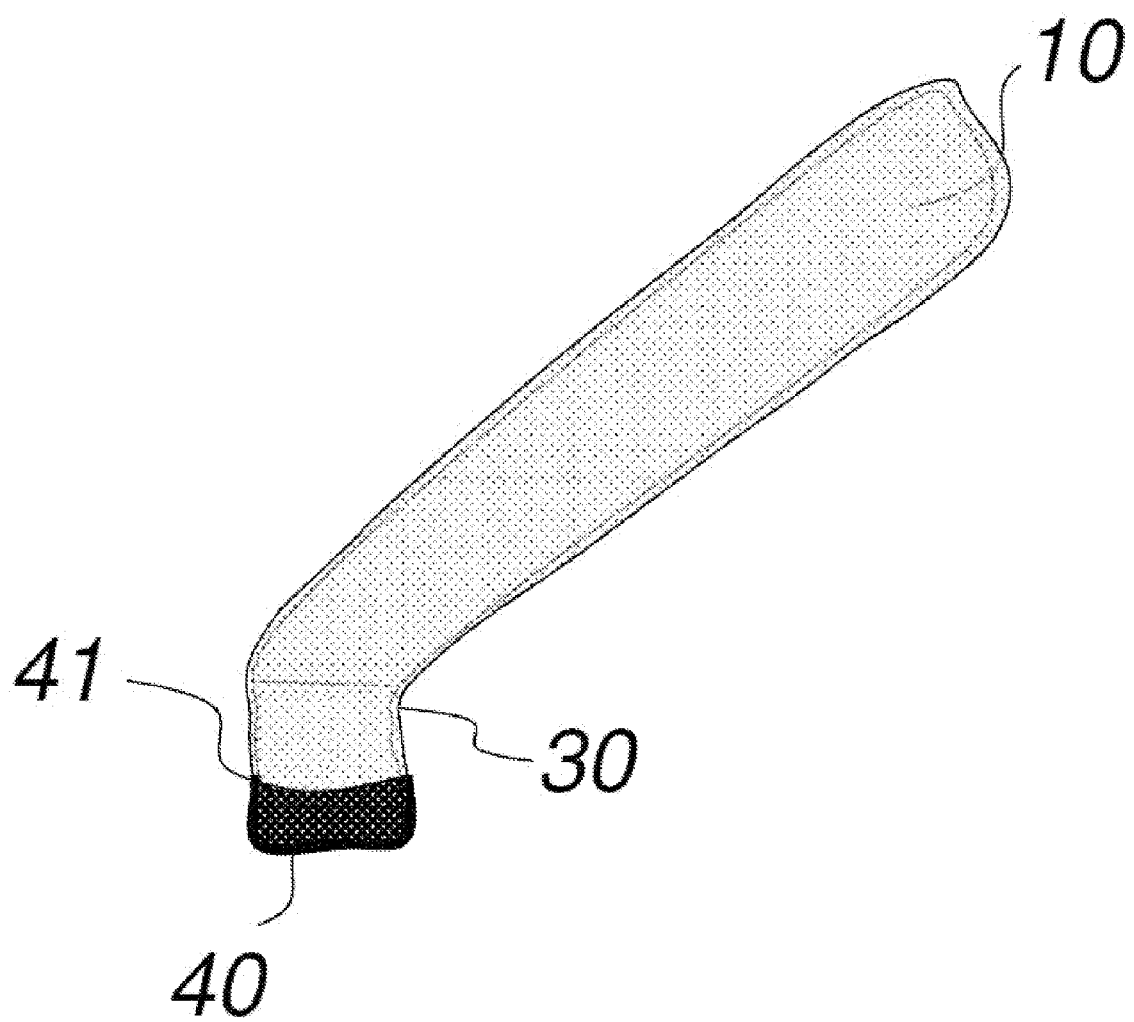
FIG. 6 is a cross section through a portion of a sterile enclosure having a pre-dispensed gel covered by a removable protective layer in a portion to be positioned adjacent a transducer.

FIG. 6 is a cross section through a portion of a sterile enclosure 30 having a pre-dispensed acoustic gel 40 covered by a removable protective layer 41 in a portion of enclosure 30 to be positioned adjacent a transducer 20. Protective layer 41 may be removed prior to inserting a hand-held ultrasound apparatus 10 into enclosure 30.

In other embodiments means may be provided for delivering acoustic gel to the interface between the transducer and the sterile enclosure. For example, the sterile enclosure or the hand-held ultrasound apparatus may comprise a compartment containing acoustic gel which can be extruded from the compartment into the space between the transducer and the inside of the sterile enclosure either after the hand-held ultrasound apparatus has been placed into the sterile enclosure or before or during placing the hand-held ultrasound apparatus into the sterile enclosure. The acoustic gel may ensure good acoustic contact between the transducer and the inside of the sterile enclosure. Acoustic gel may also be placed on the outside of the sterile enclosure during use to facilitate sliding of the combined ultrasound apparatus and sterile enclosure over the skin of a patient as well as to establish good ultrasonic acoustical coupling between the ultrasound apparatus and the subject.

In some cases, a hand-held ultrasound apparatus may be useful for guiding a needle to a specific location in a subject. For example, a needle may be used for taking biopsy samples of tissues from within a subject or guiding a needle into a vein, artery or other anatomical structure in the subject. In such cases, the hand-held ultrasound apparatus may be used to guide a needle, such as a biopsy needle, to a desired location in a tissue of interest which can be identified in an ultrasound image. In such cases, an apparatus according to the invention may provide a needle guide built into or attachable to the outside of the sterile enclosure or provided in a way that permits the needle guide to be clipped on to the outside of the sterile enclosure. The needle guide may, for example, comprise a holder for a needle which permits axial movement of the needle into an acoustical field of view of the ultrasound transducer such that the tissues into which the needle may be introduced by axial movement are imaged on a display of the hand-held ultrasound apparatus. The operator can thereby place the needle to acquire a biopsy sample from a desired position within the tissue with reference to an ultrasound image displayed on the display of the hand-held ultrasound apparatus.

Figure 7:
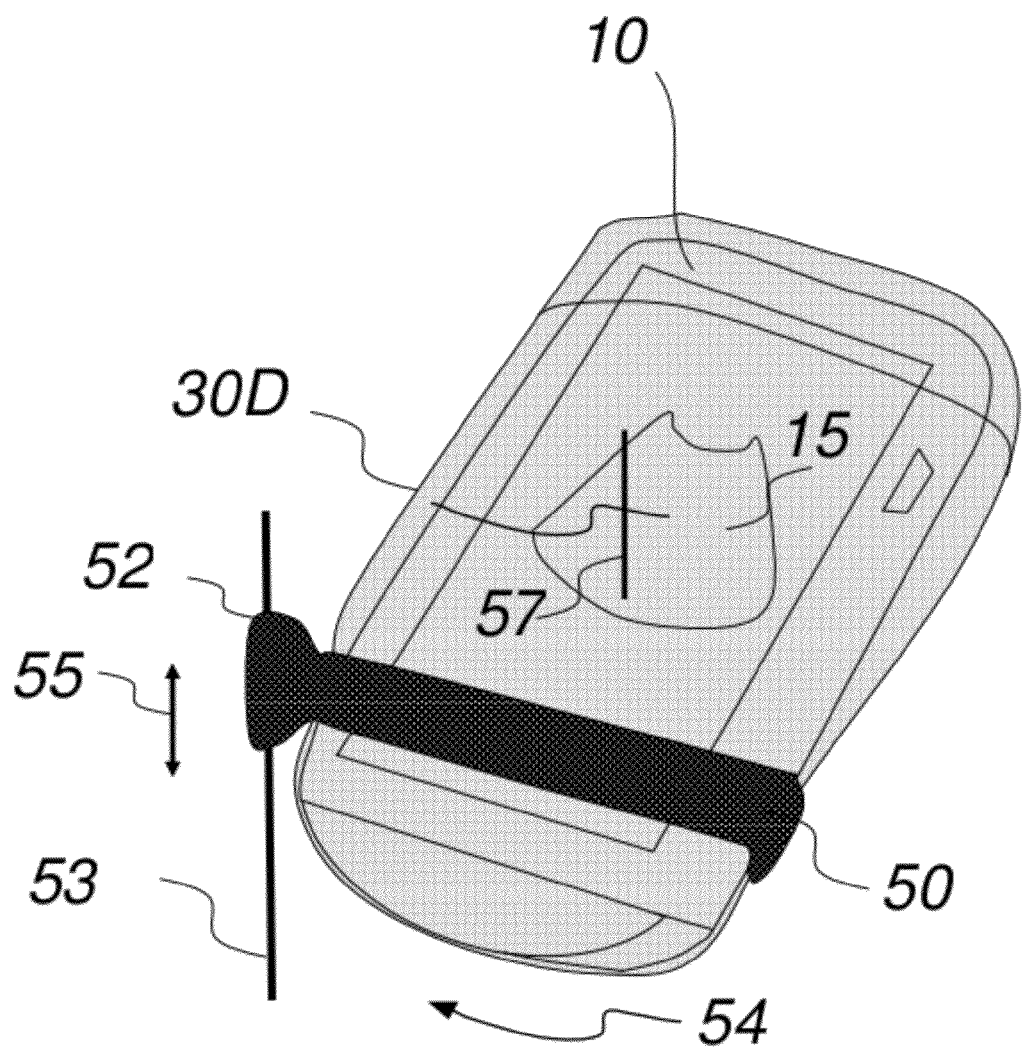
FIG. 7 shows a sterile enclosure equipped with an integrated needle guide.

FIG. 7 shows a sterile enclosure 30D equipped with an integrally formed needle guide 50. Needle guide 50 comprises a bore 52 that is aligned so that a needle 53 extending through bore 52 projects into a field of view 54 of a transducer 20 of an ultrasound apparatus 10 within sterile enclosure 30D. Needle 53 can move axially within bore 52 as indicated by arrow 55. Ultrasound apparatus 10 may be configured to overlay on an ultrasound image 15 a line or other indicia 57 indicating the path along which needle 53 can be advanced (which is constrained by needle guide 50). An operator can position the ultrasound apparatus 10 so that an anatomical structure of interest seen in image 15 intersects indicia 57. The operator can then advance needle 53 to a desired location to take a biopsy or the like. The operator can monitor the advance of needle 52 in ultrasound image 15.

Figure 8:
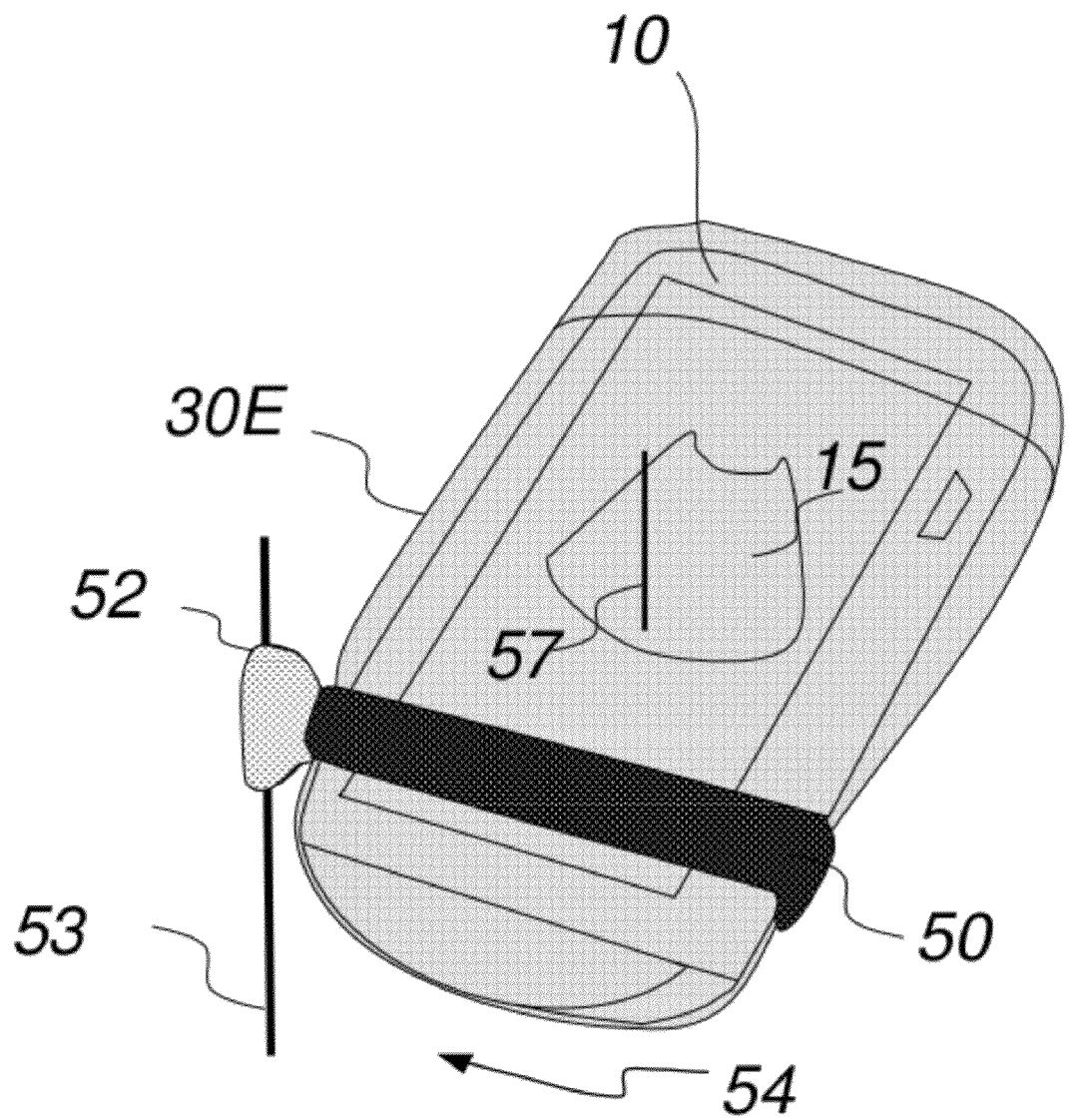
FIG. 8 shows a sterile enclosure equipped with a removable needle guide.

FIG. 8 shows a sterile enclosure 30E similar to sterile enclosure 50D of FIG. 7 except that needle guide 50 is detachable.

A sterile enclosure may be shipped inside-out to facilitate applying the sterile enclosure over an ultrasound apparatus without rendering what will be the exposed outer surface of the sterile enclosure non-sterile through contact with the ultrasound apparatus or a person's non-sterile glove or hand.

It can be seen that embodiments of this invention provide:
  sterile enclosures for hand-held ultrasound units;
  combinations of a hand-held ultrasound unit with a sterile enclosure enclosing and covering the hand-held ultrasound unit to permit use of the hand-held ultrasound unit in a sterile environment; and,
  methods for using a hand-held ultrasound unit which involve encasing the hand-held ultrasound unit in a sterile enclosure prior to use such that a display of the hand-held ultrasound unit can be viewed through the sterile enclosure, controls of the hand-held ultrasound unit can be manipulated through the sterile enclosure, and acoustic signals can be transmitted from the hand-held ultrasound unit through the sterile enclosure into a subject and reflections of those transmitted signals can be passed backed to the hand-held ultrasound unit through the sterile enclosure.

While a number of exemplary aspects and embodiments have been discussed above, those of skill in the art will recognize certain modifications, permutations, additions and sub-combinations thereof. It is therefore intended that the claims hereafter introduced may cover and should be interpreted to include all such modifications, permutations, additions and sub-combinations as are within their true spirit and scope.

What is claimed is:

1. An apparatus comprising:
   a cordless, hand-held ultrasound device comprising a display to display ultrasound images, touch sensitive controls configured to adjust settings of the hand-held ultrasound device, and a transducer comprising a transducer array, the transducer configured to transmit ultrasonic pulses into a subject and to receive reflected ultrasonic pulses which have been reflected at locations within the subject; and
   a sterile enclosure completely enclosing the hand-held ultrasound device such that any material on the hand-held ultrasound apparatus is prevented by the sterile enclosure from contaminating a sterile environment in which the hand-held ultrasound device is used while in the sterile enclosure, the enclosure comprising:
     an opening for insertion of the hand-held ultrasound device into the enclosure and removal of the hand-held ultrasound device from the enclosure;
     a closure for closing the opening;
     an acoustically-transparent transducer portion covering an active face of the transducer; and
     a transparent display portion overlaying the display of the hand-held ultrasound device to permit viewing of the display through the transparent display portion, the display portion sealed to the transducer portion to maintain sterility;
   wherein:
     the transducer portion of the enclosure comprises a semi-rigid gel pad shaped to conform to the active face of the transducer;
     the gel pad comprises a material that holds its shape and is formed with projections and/or recesses configured for engagement with corresponding recesses and/or projections on the ultrasound device;
     the enclosure comprises flexible portions overlaying the touch-sensitive controls; and
     the enclosure has a shape that conforms to features of configuration of the hand-held ultrasound device.

2. An apparatus according to claim 1, comprising a needle guide attachable to the enclosure, the needle guide having a bore for receiving a needle, the bore aligned relative to a position of the transducer in the enclosure so that the needle is projectable into a field of view of the transducer.

3. An apparatus according to claim 1, wherein the enclosure comprises an integrally formed needle guide, the needle guide having a bore for receiving a needle, the bore aligned relative to a position of the transducer in the enclosure so that the needle is projectable into a field of view of the transducer.

4. An apparatus according to claim 1 wherein the hand-held ultrasound device comprises a microphone and voice-recognition apparatus and is configured to be controlled in response to voice or other sound commands received through the sterile enclosure.

5. An apparatus according to claim 1 wherein the sterile enclosure comprises elastic material stretched over the display of the hand-held ultrasound device.

* * * * *